United States Patent
Higashi et al.

(10) Patent No.: US 12,162,854 B2
(45) Date of Patent: Dec. 10, 2024

(54) PRODUCTION METHOD FOR FLUOROMETHYL DERIVATIVE

(71) Applicants: DAIKIN INDUSTRIES, LTD., Osaka (JP); SAGA UNIVERSITY, Saga (JP)

(72) Inventors: Masahiro Higashi, Osaka (JP); Yosuke Kishikawa, Osaka (JP); Tsugio Kitamura, Saga (JP)

(73) Assignees: DAIKIN INDUSTRIES, LTD., Osaka (JP); SAGA UNIVERSITY, Saga (JP)

( * ) Notice: Subject to any disclaimer, the term of this patent is extended or adjusted under 35 U.S.C. 154(b) by 911 days.

(21) Appl. No.: 17/054,397

(22) PCT Filed: May 10, 2019

(86) PCT No.: PCT/JP2019/018748
§ 371 (c)(1),
(2) Date: Nov. 10, 2020

(87) PCT Pub. No.: WO2019/216415
PCT Pub. Date: Nov. 14, 2019

(65) Prior Publication Data
US 2021/0206740 A1 Jul. 8, 2021

(30) Foreign Application Priority Data
May 11, 2018 (JP) ................. 2018-092086

(51) Int. Cl.
| | |
|---|---|
| C07C 49/233 | (2006.01) |
| C07C 45/67 | (2006.01) |
| C07C 201/12 | (2006.01) |
| C07C 231/12 | (2006.01) |
| C07D 333/22 | (2006.01) |
| C07C 49/813 | (2006.01) |
| C07C 205/45 | (2006.01) |
| C07C 233/33 | (2006.01) |

(52) U.S. Cl.
CPC ............ *C07D 333/22* (2013.01); *C07C 45/67* (2013.01); *C07C 201/12* (2013.01); *C07C 231/12* (2013.01); *C07C 49/813* (2013.01); *C07C 205/45* (2013.01); *C07C 233/33* (2013.01)

(58) Field of Classification Search
CPC ............................ C07C 49/233; C07C 49/697
USPC ................................................ 568/308, 310
See application file for complete search history.

(56) References Cited

U.S. PATENT DOCUMENTS

2008/0125589 A1  5/2008 Ishii et al.

FOREIGN PATENT DOCUMENTS

| | | |
|---|---|---|
| JP | 2014-201553 | 10/2014 |
| JP | 2015-157788 | 9/2015 |

OTHER PUBLICATIONS

Isabel, Elise et al., "The discovery of MK-0674, an orally bioavailable cathepsin K inhibitor", Bioorganic & Medicinal Chemistry Letters, vol. 20, 2010, pp. 887-892.
Philippe Bey et al., "Communications to the Editor", Journal of Medicinal Chemistry, 1984, vol. 27, No. 1, pp. 9-10.
International Preliminary Report on Patentability issued Nov. 17, 2020 in International Patent Application No. PCT/JP2019/018748.
Extended European Search Report issued Apr. 8, 2022 in corresponding European Patent Application No. 19800180.2.
Guillaume de Nanteuil, "A Novel Access to 4-Fluoropyrimidines from α-Chloro-α'-Trifluoromethylketones", Tetrahedron Letters, vol. 32, No. 22, 1991, pp. 2467-2468.
Umemoto T., et al., "A new method for the preparation of α-(perfluoroalkyl) carbonyl and γ-(perfluoroalkyl)-α, β-unsaturated carbonyl compounds", Tetrahedron Letters, vol. 23, No. 14, Jan. 1, 1982, pp. 1471-1474.
He, M. et al., "α-Hydroxy Ketone Precursors Leading to a Novel Class of Electro-optic Acceptors", Chemistry of Materials, vol. 14, No. 5, 2002, pp. 2393-2400.
International Search Report issued Jul. 30, 2019 in International (PCT) Application No. PCT/JP2019/018748.
Banik et al., "Catalytic, asymmetric difluorination of alkenes to generate difluoromethylated stereocenters", Science, 2016, vol. 353, No. 6294, pp. 51-54.
Demir et al., "Catalytic Intermolecular Aldehyde-Ketone Coupling via Acyl Phosphonates", Journal of Organic Chemistry, 2009, vol. 74, No. 5, pp. 2197-2199.
Kitamura et al., "Difluorination of Functionalized Aromatic Olefins Using Hypervalent Iodine/HF Reagents", Journal of Organic Chemistry, 2018, vol. 83, No. 24, pp. 14853-14860.

*Primary Examiner* — Charanjit Aulakh
(74) *Attorney, Agent, or Firm* — WENDEROTH, LIND & PONACK, L.L.P.

(57) ABSTRACT

A method for producing a fluoromethyl derivative represented by formula (1), the method including step A of reacting an alkene compound represented by formula (2) with a fluorine source represented by formula $MF_n$, in the presence of a hypervalent-iodine aromatic compound (1a), or in the presence of an aromatic iodine compound (1b) and an oxidant (A) to fluorinate the alkene compound.

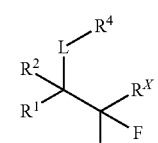

(1)

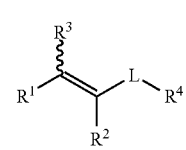

(2)

4 Claims, No Drawings

PRODUCTION METHOD FOR FLUOROMETHYL DERIVATIVE

TECHNICAL FIELD

The present disclosure relates to a method for producing a fluoromethyl derivative.

BACKGROUND ART

Typically, difluoromethyl derivatives are produced by using an expensive difluoromethylation agent (e.g., $CHF_2SO_2Cl$). As a method for producing a fluoromethyl derivative without using a difluoromethylation agent, PTL 1 suggests a method for producing a 2-fluoro-1,3-dicarbonyl compound at high yield and high selectivity. The method of PTL 1 includes reacting a 1,3-dicarbonyl compound represented by the following formula (1):

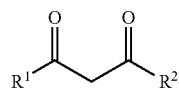

(1)

with a hydrogen fluoride source and an oxidant in the presence of an iodobenzene derivative in a catalyst amount to obtain a compound represented by the following formula (3):

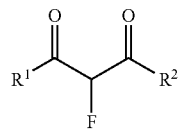

(3)

CITATION LIST

Patent Literature

PTL 1: JP2014-201553A

SUMMARY OF INVENTION

Technical Problem

An object of the present disclosure is to provide a novel method for producing a fluoromethyl derivative.

Solution to Problem

The present disclosure includes the following subject matter.

Item 1

A method for producing a fluorinated organic compound represented by formula (1):

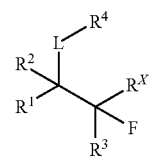

(1)

wherein
$R^1$ represents an organic group,
$R^2$ represents hydrogen, halogen, or an organic group,
$R^3$ represents hydrogen, halogen, or an organic group,
L represents a single bond, alkanediyl, —CO—, —CONR—, —NRCO—,
—O—CO—, or —CO—O— wherein R independently represents, in each occurrence, hydrogen or an organic group,
$R^4$ represents hydrogen, halogen, hydroxyl, or an organic group,
$R^3$ and $R^4$ may be linked to each other, and
$R^X$ represents hydrogen or fluoro,
provided that when $R^4$ represents hydrogen, L represents —CO—,
—CONR—, —NRCO—, —O—CO—, or —CO—O—,
the method comprising step A of reacting an alkene compound represented by formula (2):

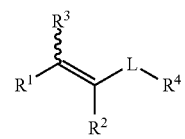

(2)

wherein the steric configuration of a single bond indicated by a wavy line with respect to a double bond to which the single bond is connected is in E configuration or Z configuration, or a mixture of E configuration and Z configuration in any ratio, and other alphabetical symbols are as defined above,
with a fluorine source that is a fluorine source (3a) represented by formula $MF_n$ wherein M represents H, a metal of Group 1 of the periodic table, or a metal of Group 2 of the periodic table; and n is 1 or 2
in the presence of a hypervalent-iodine aromatic compound (1a), or
in the presence of an aromatic iodine compound (1b) and an oxidant (A) to fluorinate the alkene compound.

Item 2

The production method according to Item 1, wherein $R^1$ represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents.

Item 3

The production method according to Item 2, wherein $R^1$ represents an aromatic hydrocarbon group optionally having one or more substituents or an aromatic heterocyclic group optionally having one or more substituents.

Item 4

The production method according to any one of Items 1 to 3, wherein $R^2$ represents hydrogen.

Item 5

The production method according to any one of Items 1 to 4, wherein $R^3$ represents hydrogen.

Item 6

The production method according to any one of Items 1 to 5, wherein L represents $-[C(-R^{4a})(-R^{4b})]_m-$,
$R^{4a}$ represents hydrogen or an organic group,
$R^{4b}$ represents hydrogen or an organic group, and
m represents an integer of 1 to 10.

Item 7

The production method according to Item 6, wherein $R^4$ represents hydroxyl.

Item 8

The production method according to any one of Items 1 to 5, wherein L represents $-CO-$, and $R^4$ represents hydrogen, halogen, or an organic group.

Item 9

The production method according to Item 8, wherein $R^4$ represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents.

Item 10

The production method according to any one of Items 1 to 5, wherein L represents $-CO-O-$, and $R^4$ represents hydrogen or an organic group.

Item 11

The production method according to Item 10, wherein $R^4$ represents a $C_{1-10}$ aliphatic hydrocarbon group optionally having one or more substituents.

Item 12

The production method according to any one of Items 1 to 11, wherein $R^X$ represents fluoro.

Item 13

The production method according to any one of Items 1 to 11, wherein $R^X$ represents hydrogen.

Item 14

A fluorinated organic compound represented by formula (1-1):

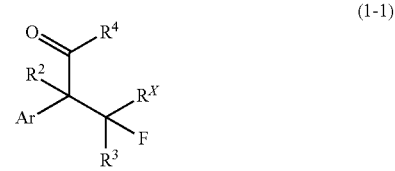

(1-1)

wherein
Ar represents an aromatic hydrocarbon group optionally having one or more substituents or an aromatic heterocyclic group optionally having one or more substituents;
$R^2$ represents hydrogen, halogen, or an organic group;
$R^3$ represents hydrogen, halogen, or an organic group;
$R^4$ represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents,
$R^3$ and $R^4$ may be linked to each other, and
$R^X$ represents hydrogen or fluoro.

Item 15

The fluorinated organic compound according to Item 14, wherein $R^X$ represents fluoro.

Item 16

The fluorinated organic compound according to Item 14, wherein $R^X$ represents hydrogen.

Advantageous Effects of Invention

The present disclosure provides a novel method for producing a fluoromethyl derivative.

DESCRIPTION OF EMBODIMENTS

1. Term

The symbols and abbreviations in the present specification can be understood in the sense commonly used in the technical field to which the present disclosure pertains in the context of the present specification, unless otherwise specified.

In the present specification, the terms "comprise" and "contain" are used with the intention of including the phrases "consist essentially of" and "consist of."

Unless otherwise specified, the steps, treatments, and operations described in the present specification can be performed at room temperature.

In the present specification, "room temperature" means a temperature within the range of 10 to 40° C.

In the present specification, the phrase "$C_n$-$C_m$" (n and m each represent a number) indicates that the number of carbon atoms is n or more and m or less, as can typically be understood by a person skilled in the art.

In the present specification, the phrase "organic compound" is understood in the ordinary sense, and can be a compound having one or more carbon atoms and one or more hydrogen atoms.

In the present specification, the phrase "organic group" refers to a group having one or more carbon atoms (or a group formed by removing one hydrogen atom from an organic compound).

In the present specification, the fluorinated organic compound refers to a compound that can be formed by fluorinating an organic compound, and may contain no hydrogen atoms.

In the present specification, unless otherwise specified, examples of halogen (groups) may include fluoro (group), chloro (group), bromo (group), and iodine (group).

In the present specification, examples of aromatic rings include aromatic carbocyclic rings and aromatic heterocyclic rings. In the present specification, "aromatic compound" refers to a compound having one or more aromatic rings.

In the present specification, unless otherwise specified, examples of aromatic carbocyclic rings include aromatic hydrocarbon rings having 6 to 14 carbon atoms, and specific examples include benzene, naphthalene, anthracene, phenanthrene, and biphenyl.

In the present specification, unless otherwise specified, examples of aromatic heterocyclic rings include 5- or 6-membered aromatic heterocyclic rings; and specific examples include a furan ring, a thiophene ring, a pyrrole ring, an oxazole ring, an isoxazole ring, a thiazole ring, an isothiazole ring, an imidazole ring, a pyrazole ring, a 1,2,3-oxadiazole ring, a 1,2,4-oxadiazole ring, a 1,3,4-oxadiazole ring, a furazan ring, a 1,2,3-thiadiazole ring, a 1,2,4-thiadiazole ring, a 1,3,4-thiadiazole ring, a 1,2,3-triazole ring, a 1,2,4-triazole ring, a tetrazole ring, a pyridine ring, a pyridazine ring, a pyrimidine ring, a pyrazine ring, and a triazine ring.

In the present specification, unless otherwise specified, other examples of aromatic heterocyclic rings include a condensed ring of one or more 5- or 6-membered aromatic heterocyclic rings and one or more aromatic carbocyclic rings.

Examples of organic groups include:
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents,
a non-aromatic heterocyclic group optionally having one or more substituents,
a heteroaryl group optionally having one or more substituents,
a cyano group,
an aldehyde group,
R'O—,
R'CO—,
R'SO$_2$—,
R'OCO—, and
R'OSO$_2$—

(in these formulas, R' is independently
an alkyl group optionally having one or more substituents,
an alkenyl group optionally having one or more substituents,
an alkynyl group optionally having one or more substituents,
a cycloalkyl group optionally having one or more substituents,
a cycloalkenyl group optionally having one or more substituents,
a cycloalkadienyl group optionally having one or more substituents,
an aryl group optionally having one or more substituents,
an aralkyl group optionally having one or more substituents,
a non-aromatic heterocyclic group optionally having one or more substituents, or
a heteroaryl group optionally having one or more substituents).

In the present specification, the organic group may be, for example, a hydrocarbon group optionally having one or more substituents (to the hydrocarbon group, one or more moieties selected from the group consisting of —NR$^o$—, =N—, —N=, —O—, —S—, —C(=O)O—, —OC(=O)—, —C(=O)—, —S(=O)—, —S(=O)$_2$—, —S(=O)$_2$—NR$^o$—, —NR$^o$—S(=O)$_2$—, —S(=O)—, —S(=O)—NR$^o$—, and —NR$^o$—S(=O)— (wherein R$^o$ is independently a hydrogen atom or an organic group) may be introduced).

As can be typically understood based on common knowledge in the field of chemistry, examples of hydrocarbon groups with a heteroatom thus introduced include non-aromatic heterocyclic groups and heteroaryl groups.

In the present specification, the number of carbon atoms in the "hydrocarbon group" of the "hydrocarbon group optionally having one or more substituents" may be, for example, 1 to 100, 1 to 80, 1 to 60, 1 to 40, 1 to 30, 1 to 20, or 1 to 10 (e.g., 1, 2, 3, 4, 5, 6, 7, 8, 9, or 10).

In the present specification, examples of substituents in the "hydrocarbon group optionally having one or more substituents," "alkyl group optionally having one or more substituents," "alkenyl group optionally having one or more substituents," "alkynyl group optionally having one or more substituents," "cycloalkyl group optionally having one or more substituents," "cycloalkenyl group optionally having one or more substituents," "cycloalkadienyl group optionally having one or more substituents," "aryl group optionally having one or more substituents," and "aralkyl group optionally having one or more substituents" include a halo group, a nitro group, a cyano group, an oxo group, a thioxo group, a sulfo group, a sulfamcyl group, a sulfinamoyl group, and a sulfenamoyl group.

The number of substituents may be within the range of 1 to the maximum substitutable number (e.g., 1, 2, 3, 4, 5, or 6).

In the present specification, examples of hydrocarbon groups include an alkyl group, an alkenyl group, an alkynyl group, a cycloalkyl group, a cycloalkenyl group, a cycloalkadienyl group, an aryl group, an aralkyl group, and a group that is a combination of these groups.

In the present specification, unless otherwise specified, examples of alkyl groups include linear or branched $C_1$-$C_{10}$ alkyl groups, such as methyl, ethyl, propyl, isopropyl, butyl (n-butyl, isobutyl, sec-butyl, tert-butyl), pentyl (n-pentyl, isopentyl, neopentyl), hexyl, heptyl, octyl, nonyl, and decyl.

In the present specification, a fluoroalkyl group refers to an alkyl group in which at least one hydrogen atom is replaced by a fluorine atom.

In the present specification, the number of fluorine atoms in a fluoroalkyl group may be one or more (e.g., 1 to 3, 1 to 6, 1 to 12, or 1 to the maximum substitutable number).

As can be understood by a person skilled in the art, the prefix "perhalogeno" means that all hydrogen atoms are replaced by a halogen group.

As can be understood by a person skilled in the art, the prefix "perfluoro" means that all hydrogen atoms are replaced by a fluoro group.

A fluoroalkyl group includes a perfluoroalkyl group.

A perfluoroalkyl group is an alkyl group in which all hydrogen atoms are replaced by a fluorine atom. Specific examples of perfluoroalkyl groups include a trifluoromethyl group ($CF_3$—) and a pentafluoroethyl group ($C_2F_5$—).

In the present specification, a fluoroalkyl group may be, for example, a fluoroalkyl group having 1 to 20, 1 to 12, 1 to 6, 1 to 4, 1 to 3, 6, 5, 4, 3, 2, or 1 carbon atom.

In the present specification, the fluoroalkyl group may be a linear or branched fluoroalkyl group.

In the present specification, specific examples of fluoroalkyl groups include a fluoromethyl group, a difluoromethyl group, a trifluoromethyl group ($CF_3$—), a 2,2,2-trifluoroethyl group, a pentafluoroethyl group ($C_2F_5$—), a tetrafluoropropyl group (e.g., $HCF_2CF_2CH_2$—), a hexafluoropropyl group (e.g., $(CF_3)_2CH$—), a nonafluorobutyl group, an octafluoropentyl group (e.g., $HCF_2CF_2CF_2CF_2CH_2$—), a tridecafluorohexyl group, and a 3,3,4,4,5,5,6,6,7,7,8,8,8-tridecafluorooctyl group ($CF_3CF_2CF_2CF$—$CF_2CF_2CH_2CH_2$—).

In the present specification, unless otherwise specified, examples of alkenyl groups include linear or branched $C_{2-10}$ alkenyl groups, such as vinyl, 1-propen-1-yl, 2-propen-1-yl, isopropenyl, 2-buten-1-yl, 4-penten-1-yl, and 5-hexen-1-yl.

In the present specification, unless otherwise specified, examples of alkynyl groups include linear or branched $C_2$-$C_{10}$ alkynyl groups, such as ethynyl, 1-propyn-1-yl, 2-propyn-1-yl, 4-pentyn-1-yl, and 5-hexyn-1-yl.

In the present specification, unless otherwise specified, examples of cycloalkyl groups include $C_3$-$C_7$ cycloalkyl groups, such as cyclopropyl, cyclobutyl, cyclopentyl, cyclohexyl, and cycloheptyl.

In the present specification, unless otherwise specified, examples of cycloalkenyl groups include $C_3$-$C_7$ cycloalkenyl groups, such as cyclopropenyl, cyclobutenyl, cyclopentenyl, cyclohexenyl, and cycloheptenyl.

In the present specification, unless otherwise specified, examples of cycloalkadienyl groups include $C_4$-$C_{10}$ cycloalkadienyl groups, such as cyclobutadienyl, cyclopentadienyl, cyclohexadienyl, cycloheptadienyl, cyclooctadienyl, cyclononadienyl, and cyclodecadienyl.

In the present specification, unless otherwise specified, aromatic groups include an aryl group and an heteroaryl group.

In the present specification, unless otherwise specified, the aryl group may be monocyclic, bicyclic, tricyclic, or tetracyclic.

In the present specification, unless otherwise specified, the aryl group may be a $C_6$-$C_{18}$ aryl group.

In the present specification, unless otherwise specified, examples of aryl groups include phenyl, 1-naphthyl, 2-naphthyl, 2-biphenyl, 3-biphenyl, 4-biphenyl, and 2-anthryl.

In the present specification, unless otherwise specified, examples of aralkyl groups include benzyl, phenethyl, diphenylmethyl, 1-naphthylmethyl, 2-naphthylmethyl, 2,2-diphenylethyl, 3-phenylpropyl, 4-phenylbutyl, 5-phenylpentyl, 2-biphenylylmethyl, 3-biphenylylmethyl, and 4-biphenylylmethyl.

In the present specification, unless otherwise specified, a non-aromatic heterocyclic group may be menocyclic, bicyclic, tricyclic, or tetracyclic.

In the present specification, unless otherwise specified, the non-aromatic heterocyclic group may be, for example, a non-aromatic heterocyclic group that contains, as ring-constituting atom(s), 1 to 4 heteroatoms selected from an oxygen atom, a sulfur atom, or a nitrogen atom, in addition to a carbon atom.

In the present specification, unless otherwise specified, the non-aromatic heterocyclic group may be saturated or unsaturated.

In the present specification, unless otherwise specified, examples of non-aromatic heterocyclic groups include tetrahydrofuryl, oxazolidinyl, imidazolinyl (e.g., 1-imidazolinyl, 2-imidazolinyl, and 4-imidazolinyl), aziridinyl (e.g., 1-aziridinyl and 2-aziridinyl), azetidinyl (e.g., 1-azetidinyl and 2-azetidinyl), pyrrolidinyl (e.g., 1-pyrrolidinyl, 2-pyrrolidinyl, and 3-pyrrolidinyl), piperidinyl (e.g., 1-piperidinyl, 2-piperidinyl, and 3-piperidinyl), azepanyl (e.g., 1-azepanyl, 2-azepanyl, 3-azepanyl, and 4-azepanyl), azocanyl (e.g., 1-azocanyl, 2-azocanyl, 3-azocanyl, and 4-azocanyl), piperazinyl (e.g., 1,4-piperazin-1-yl and 1,4-piperazin-2-yl), diazepinyl (e.g., 1,4-diazepin-1-yl, 1,4-diazepin-2-yl, 1,4-diazepin-5-yl, and 1,4-diazepin-6-yl), diazocanyl (e.g., 1,4-diazocan-1-yl, 1,4-diazocan-2-yl, 1,4-diazocan-5-yl, 1,4-diazocan-6-yl, 1,5-diazocan-1-yl, 1,5-diazocan-2-yl, and 1,5-diazocan-3-yl), tetrahydropyranyl (e.g., tetrahydropyran-4-yl), morpholinyl (e.g., 4-morpholinyl), thiomorpholinyl (e.g., 4-thiomorpholinyl), 2-oxazolidinyl, dihydrofuryl, dihydropyranyl, and dihydroquinolyl.

In the present specification, unless otherwise specified, examples of heteroaryl groups include monocyclic aromatic heterocyclic groups (e.g., 5- or 6-membered monocyclic aromatic heterocyclic groups) and aromatic condensed heterocyclic groups (e.g., 5- to 18-membered aromatic condensed heterocyclic groups).

In the present specification, unless otherwise specified, examples of 5- or 6-membered monocyclic aromatic heterocyclic groups include pyrrolyl (e.g., 1-pyrrolyl, 2-pyrrolyl, and 3-pyrrolyl), furyl (e.g., 2-furyl and 3-furyl), thienyl (e.g., 2-thienyl and 3-thienyl), pyrazolyl (e.g., 1-pyrazolyl, 3-pyrazolyl, and 4-pyrazolyl), imidazolyl (e.g., 1-imidazolyl, 2-imidazolyl, and 4-imidazolyl), isoxazolyl (e.g., 3-isoxazolyl, 4-isoxazolyl, and 5-isoxazolyl), oxazolyl (e.g., 2-oxazolyl, 4-oxazolyl, and 5-oxazolyl), isothiazolyl (e.g., 3-isothiazolyl, 4-isothiazolyl, and 5-isothiazolyl), thiazolyl (e.g., 2-thiazolyl, 4-thiazolyl, and 5-thiazolyl), triazolyl (e.g., 1,2,3-triazol-4-yl and 1,2,4-triazol-3-yl), oxadiazolyl (e.g., 1,2,4-oxadiazol-3-yl and 1,2,4-oxadiazol-5-yl), thiadiazolyl (e.g., 1,2,4-thiadiazol-3-yl and 1,2,4-thiadiazol-5-yl), tetrazolyl, pyridyl (e.g., 2-pyridyl, 3-pyridyl, and 4-pyridyl), pyridazinyl (e.g., 3-pyridazinyl and 4-pyridazinyl), pyrimidinyl (e.g., 2-pyrimidinyl, 4-pyrimidinyl, and 5-pyrimidinyl), and pyrazinyl.

In the present specification, unless otherwise specified, examples of 5- to 18-membered aromatic condensed heterocyclic groups include isoindolyl (e.g., 1-isoindolyl, 2-isoindolyl, 3-isoindolyl, 4-isoindolyl, 5-isoindolyl, 6-isoindolyl, and 7-isoindolyl), indolyl (e.g., 1-indolyl, 2-indolyl, 3-indolyl, 4-indolyl, 5-indolyl, 6-indolyl, and 7-indolyl), benzo[b]furanyl (e.g., 2-benzo[b]furanyl, 3-benzo[b]furanyl, 4-benzo[b]furanyl, 5-benzo[b]furanyl, 6-benzo[b]furanyl, and 7-benzo[b]furanyl), benzo[c]furanyl (e.g., 1-benzo[c]furanyl, 4-benzo[c]furanyl, and 5-benzo[c]furanyl), benzo[b]thienyl (e.g., 2-benzo[b]thienyl, 3-benzo[b]thienyl, 4-benzo[b]thienyl, 5-benzo[b]thienyl, 6-benzo[b]thienyl, and 7-benzo[b]thienyl), benzo[c]thienyl (e.g., 1-benzo[c]thienyl, 4-benzo[c]thienyl, and 5-benzo[c]thienyl), indazolyl (e.g., 1-indazolyl, 2-indazolyl, 3-indazolyl, 4-indazolyl, 5-indazolyl, 6-indazolyl, and 7-indazolyl), benzimidazolyl (e.g., 1-benzimidazolyl, 2-benzimidazolyl, 4-benzimidazolyl, and 5-benzimidazolyl), 1,2-benzisoxazolyl (e.g., 1,2-benzisoxazol-3-yl, 1,2-benzisoxazol-4-yl, 1,2-benzisoxazol-5-yl, 1,2-benzisoxazol-6-yl, and 1,2-benzisoxazol-7-yl), benzoxazolyl (e.g., 2-benzoxazolyl, 4-benzoxazolyl, 5-benzoxazolyl, 6-benzoxazolyl, and 7-benzoxazolyl), 1,2-benzisothiazolyl (e.g., 1,2-benzisothiazol-3-yl, 1,2-benzisothiazol-4-yl, 1,2-benzisothiazol-5-yl, 1,2-benzisothiazol-6-yl, and 1,2-benzisothiazol-7-yl), benzothiazolyl (e.g., 2-benzothiazolyl, 4-benzothiazolyl, 5-benzothiazolyl, 6-benzothiazolyl, and 7-benzothiazolyl), isoquinolyl (e.g., 1-isoquinolyl, 3-isoquinolyl, 4-isoquinolyl, and 5-isoquinolyl), quinolyl (e.g., 2-quinolyl, 3-quinolyl, 4-quinolyl, 5-quinolyl, and 8-quinolyl), cinnolinyl (e.g., 3-cinnolinyl, 4-cinnolinyl, 5-cinnolinyl, 6-cinnolinyl, 7-cinnolinyl, and 8-cinnolinyl), phthalazinyl (e.g., 1-phthalazinyl, 4-phthalazinyl, 5-phthalazinyl, 6-phthalazinyl, 7-phthalazinyl, and 8-phthalazinyl), quinazolinyl (e.g., 2-quinazolinyl, 4-quinazolinyl, 5-quinazolinyl, 6-quinazolinyl, 7-quinazolinyl, and 8-quinazolinyl), quinoxalinyl (e.g., 2-quinoxalinyl, 3-quinoxalinyl, 5-quinoxalinyl, 6-quinoxalinyl, 7-quinoxalinyl, and 8-quinoxalinyl), pyrazolo[1,5-a]pyridyl (e.g., pyrazolo[1,5-a]pyridin-2-yl, pyrazolo[1,5-a]pyridin-3-yl, pyrazolo[1,5-a]pyridin-4-yl, pyrazolo[1,5-a]pyridin-5-yl, pyrazolo[1,5-a]pyridin-6-yl, and pyrazolo[1,5-a]pyridin-7-yl), imidazo[1,2-a]pyridyl (e.g., imidazo[1,2-a]pyridin-2-yl, imidazo[1,2-a]pyridin-3-yl, imidazo[1,2-a]pyridin-5-yl, imidazo[1,2-a]pyridin-6-yl, imidazo[1,2-a]pyridin-7-yl, and imidazo[1,2-a]pyridin-8-yl).

In the present specification, unless otherwise specified, examples of substituents in the "non-aromatic heterocyclic group optionally having one or more substituents" and "heteroaryl group optionally having one or more substituents" include a hydrocarbon group optionally having one or more substituents, a halogen atom, a nitro group, a cyano group, an oxo group, a thioxo group, a sulfo group, a sulfamoyl group, a sulfinamoyl group, and a sulfenamoyl group.

The number of substituents may be within the range of 1 to the maximum substitutable number (e.g., 1, 2, 3, 4, 5, or 6).

2. A Method for Producing a Fluorinated Organic Compound

An embodiment the present disclosure is a method for producing a fluorinated organic compound represented by formula (1):

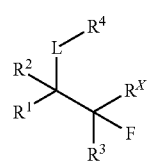

(1)

wherein
$R^1$ represents an organic group,
$R^2$ represents hydrogen, halogen, or an organic group,
$R^3$ represents hydrogen, halogen, or an organic group,
L represents a single bond, alkanediyl, —CO—, —CONR—, —NRCO—, —O—CO—, or —CO—O— wherein R independently represents, in each occurrence, hydrogen or an organic group,
$R^4$ represents hydrogen, halogen, hydroxyl, or an organic group,
$R^3$ and $R^4$ may be linked to each other, and
$R^X$ represents hydrogen or fluoro,
provided that when $R^4$ represents hydrogen, L represents —CO—,
—CONR—, —NRCO—, —O—CO—, or —CO—O—,
the method comprising step A of reacting an alkene compound represented by formula (2):

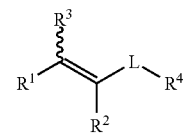

(2)

wherein the steric configuration of a single bond indicated by a wavy line with respect to a double bond to which the single bond is connected is in E configuration or Z configuration, or a mixture of E configuration and Z configuration in any ratio, and other alphabetical symbols are as defined above,
with a fluorine source that is a fluorine source (3a) represented by formula $MF_n$ wherein M represents H, a metal of Group 1 of the periodic table, or a metal of Group 2 of the periodic table; and n is 1 or 2
in the presence of a hypervalent-iodine aromatic compound (1a), or
in the presence of an aromatic iodine compound (1b) and an oxidant (A) to fluorinate the alkene compound.

$R^1$ preferably represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents.

$R^1$ more preferably represents an aromatic hydrocarbon group optionally having one or more substituents or an aromatic heterocyclic group optionally having one or more substituents.

$R^1$ still more preferably represents a $C_{6-14}$ aromatic hydrocarbon group optionally having one or more substituents or a 5- to 14-membered aromatic heterocyclic group optionally having one or more substituents.

$R^1$ even still more preferably represents a $C_{6-14}$ aryl group optionally having one or more substituents selected from the group consisting of halogen, $C_{1-6}$ alkyl, $C_{1-6}$ alkoxy, and nitro (e.g., 1, 2, 3, 4, 5, or 6 substituents) or a 5- to 14-membered aromatic heterocyclic group optionally having one or more substituents selected from the group consisting of halogen, $C_{1-6}$ alkyl, $C_{1-6}$ alkoxy, and nitro (e.g., 1, 2, 3, 4, 5, or 6 substituents).

$R^3$ preferably represents hydrogen or $C_{1-6}$ alkyl.
$R^2$ preferably represents hydrogen.

When $R^3$ and $R^4$ are linked to each other, any atom of $R^3$ (e.g., the atom in the terminal or an internal atom) and any atom of $R^4$ (e.g., the atom in the terminal or an internal atom) may link to each other.

When $R^3$ and $R^4$ are linked to each other, the part represented by "$R^3$—C—C-L-$R^4$" in formula (1) may be a ring optionally having one or more substituents.

The ring may optionally have one or more substituents.

The one or more substituents may be derived from the structure or partial structure of $R^3$, L, and/or $R^4$ (e.g., substituents).

The ring may be, for example, a monocyclic, bicyclic, or tricyclic ring.

The ring may be, for example, a 5- to 14-membered ring, a 5- to 10-membered ring, a 6- to 14-membered ring, a 6- to 10-membered ring, or a 5- or 6-membered ring.

In an embodiment, preferably,
L represents —[C(—$R^{4a}$)(—$R^{4b}$)]$_m$—,
$R^{4a}$ represents hydrogen or an organic group,
$R^{4b}$ represents hydrogen or an organic group, and
m represents an integer of 1 to 10.

More preferably,
L represents —[C(—$R^{4a}$)(—$R^{4b}$)]$_m$—,
$R^{4a}$ represents hydrogen or $C_{1-6}$ alkyl,
$R^{4b}$ represents hydrogen or $C_{1-6}$ alkyl, and
m represents an integer of 1 to 6.

Still more preferably,
L represents —[C(—$R^{4a}$)(—$R^{4b}$)]$_m$—,
$R^{4a}$ represents hydrogen,
$R^{4b}$ represents hydrogen, and
m represents 1.

$R^4$ is more preferably $C_{1-10}$ alkoxy or hydroxyl. $R^4$ is still more preferably hydroxyl.

In another embodiment, preferably,
L represents —CO—, and
$R^4$ represents hydrogen, halogen, or an organic group.

$R^4$ is preferably an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents.

$R^4$ is more preferably a $C_{1-6}$ alkyl group, a phenyl group optionally having one or more substituents, a naphthyl group optionally having one or more substituents, or a thiophenyl group optionally having one or more substituents.

$R^4$ is still more preferably a $C_{1-3}$ alkyl group or a phenyl group optionally having one or more substituents.

In another embodiment, preferably,
L represents —CO—O—, and
$R^4$ represents hydrogen or an organic group.

$R^4$ is preferably an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents.

$R^4$ is more preferably a $C_{1-10}$ alkyl group. $R^4$ is still more preferably a $C_{1-6}$ alkyl group.

In an embodiment, $R^X$ is preferably fluorine. The compound in which $R^X$ is fluorine (this compound may be referred to as "difluoro form") can be produced at a higher selectivity by increasing the reaction temperature, increasing the reaction time, increasing the amount of fluorine source, or any combination of these in step A.

In another embodiment, $R^X$ is preferably hydrogen. The compound in which $R^X$ is hydrogen (this compound may be referred to as "monofluoro form") can be produced at a higher selectivity by decreasing the reaction temperature, decreasing the reaction time, decreasing the amount of fluorine source, or any combination of these in step A.

The difluoro form and the monofluoro form can be separated by a commonly used purification method, if desired.

In an embodiment according to the present disclosure, preferably,
$R^1$ is an aromatic hydrocarbon group optionally having one or more substituents or an aromatic heterocyclic group optionally having one or more substituents;
$R^3$ represents hydrogen or $C_{1-6}$ alkyl;
$R^2$ represents hydrogen;
L represents —[C(—$R^{4a}$)(—$R^b$)]$_m$—,
$R^{4a}$ represents hydrogen or an organic group,
$R^{4b}$ represents hydrogen or an organic group,
m represents an integer of 1 to 10,
$R^4$ represents hydroxyl, and
$R^X$ represents fluorine or hydrogen.

In this mode, more preferably,
$R^1$ represents a $C_{6-14}$ aryl group optionally having one or more substituents (e.g., 1, 2, 3, 4, 5, or 6 substituents) selected from the group consisting of halogen, $C_{1-6}$ alkyl, $C_{1-6}$ alkoxy, and nitro, or a 5- to 14-membered aromatic heterocyclic group optionally having one or more substituents (e.g., 1, 2, 3, 4, 5, or 6 substituents) selected from the group consisting of halogen, $C_{1-6}$ alkyl, $C_{1-6}$ alkoxy, and nitro;
$R^3$ represents hydrogen or $C_{1-6}$ alkyl;
$R^2$ represents hydrogen;
L represents —$CH_2$—;
$R^4$ represents hydroxyl; and
$R^X$ represents fluorine or hydrogen.

In another embodiment according to the present disclosure,
$R^1$ represents an aromatic hydrocarbon group optionally having one or more substituents or an aromatic heterocyclic group optionally having one or more substituents;
$R^2$ represents hydrogen;
$R^3$ represents hydrogen;
L represents —CO—,
$R^4$ represents hydrogen, halogen, or an organic group.

In a preferable embodiment,
R=represents a phenyl group optionally having one or more substituents;
$R^2$ represents hydrogen;
$R^3$ represents hydrogen;
L represents —CO—; and
$R^4$ represents a phenyl group optionally having one or more substituents.

In another embodiment according to the present disclosure, preferably,
$R^1$ represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents;
$R^2$ represents hydrogen;
$R^3$ represents hydrogen;
L represents —CO—;
$R^4$ represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents; and
$R^X$ represents fluorine or hydrogen.

In another embodiment according to the present disclosure,
$R^1$ represents an aromatic hydrocarbon group optionally having one or more substituents or an aromatic heterocyclic group optionally having one or more substituents;
$R^2$ represents hydrogen;
$R^3$ represents hydrogen;
L represents —CO—O—; and
$R^4$ represents hydrogen or an organic group.

In another embodiment according to the present disclosure, preferably,
$R^1$ represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents;
$R^2$ represents hydrogen;
$R^3$ represents hydrogen;
L represents —CO—O—;
$R^4$ represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents; and
$R^X$ represents fluorine or hydrogen.

The fluorine source for use in step A is represented by formula $MF_n$ wherein M is H, a metal of Group 1 of the periodic table, or a metal of Group 2 of the periodic table; and n is 1 or 2. M may be preferably H, Li, Na, K, Ca, or Cs; more preferably H, Na, K, or Ca; and still more preferably H. The fluorine source may be preferably a hydrogen fluoride source.

Examples of the fluorine source include anhydrous hydrofluoric acid, a hydrofluoric acid aqueous solution (e.g., an aqueous hydrofluoric acid solution with a concentration of 10 to 70 wt %), and a mixture of hydrofluoric acid, an organic base, and an inorganic base.

In this mixture, the hydrofluoric acid and organic base may be specifically, for example, salts, such as hydrogen fluoride-triethylamine salt [Et$_3$N·nHF (n=1 to 5)], hydrogen fluoride-pyridine salt [Py·nHF (n=1 to 10)], and hydrogen fluoride-tetraethylammonium fluoride salt [Et$_4$NF·nHF (n=1 to 10)]; or may be derived therefrom.

In this mixture, the hydrofluoric acid and inorganic base may be specifically, for example, HF—KF(KHF$_2$); or may be derived therefrom.

These fluorine sources can be used singly, or in combination of two or more.

The amount of hydrogen fluoride source for use may be, for example, as hydrogen fluoride, typically within the range of 0.5 to 100 mol, preferably within the range of 1 to 80 mol, more preferably within the range of 2 to 60 mol, and still more preferably within the range of 3 to 50 mol, per mol of the organic compound (2), which is the substrate.

Hypervalent-Iodine Aromatic Compound (1a)

Specific examples of hypervalent-iodine aromatic compounds (1a) include iodosylbenzene, 2-iodosyltoluene, 3-iodosyltoluene, 4-iodosyltoluene, 2,4,6-trimethyliodosylbenzene, 2-ethyliodosylbenzene, 3-ethyliodosylbenzene, 4-ethyliodosylbenzene, 2-iodosylanisole, 3-iodosylanisole, 4-iodosylanisole, 1-chloro-2-iodosylbenzene, 1-chloro-3-iodosylbenzene, 1-chloro-4-iodosylbenzene, 1,2-diiodosylbenzene, 1,3-diiodosylbenzene, 1,4-diiodosylbenzene, 1-iodosyl-2-nitrobenzene, 1-iodosyl-3-nitrobenzene, 1-iodosyl-4-nitrobenzene, 1-iodosyl-2-cyanobenzene, 1-iodosyl-3-cyanobenzene, and 1-iodosyl 4-cyanobenzene. These hypervalent-iodine aromatic compounds may be used singly, or in a combination of two or more.

The amount of the hypervalent-iodine aromatic compound (1a) may be typically 0.1 to 50 mol, and preferably 0.2 to 30 mol, per mol of the compound (2).

In step A, the hypervalent-iodine aromatic compound (1a) is preferably used in the absence of an oxidant.

"Absence of an oxidant" as used herein means that the amount of an oxidant in the reaction system in step A is 0.1 mol or less per mol of the organic compound (1).

Aromatic Iodine Compound (1b) and Oxidant (A)

Examples of the aromatic iodine compound (1b) include iodobenzene, 2-iodotoluene, 3-iodotoluene, 4-iodotoluene, 2,4,6-trimethyliodobenzene, 2-ethyliodobenzene, 3-ethyliodobenzene, 4-ethyliodobenzene, 2-iodoanisole, 3-iodoanisole, 4-iodcanisole, 1-chloro-2-iodobenzene, 1-chloro-3-iodobenzene, 1-chloro-4-iodobenzene, 1,2-diiodobenzene, 1,3-diiodobenzene, 1,4-diiodobenzene, 1-iodo-2-nitrobenzene, 1-iodo-3-nitrobenzene, 1-iodo-4-nitrobenzene, 1-iodo-2-cyanobenzene, 1-iodo-3-cyanobenzene, 1-iodo-4-cyanobenzene, 1-iodo-4-(3,3,4,4,5,5,6,6,7,7,8,8,8-tridecafluorooctyl)benzene, p-iodobenzoic acid, 2-iodopyridine, 3-iodopyridine, 4-iodopyridine, 3-iodopyrazole, and 4-iodopyrazole. These aromatic iodine compounds may be used singly, or in a combination of two or more.

The amount of the hypervalent-iodine aromatic compound (1b) may be typically 0.1 to 50 mol, and preferably 0.2 to 30 mol, per mol of the compound (2).

In step A, the aromatic iodine compound (1b) is used together with the oxidant (A).

The oxidant (A) may be preferably, for example, one or more members selected from the group consisting of:
(i) a compound represented by formula: $R^YCOOOM$ wherein $R^X$ is a hydrocarbon group optionally having one or more substituents, and
M is a hydrogen atom or a metal atom;
(ii) a compound represented by formula: $R^XOOM$ wherein $R^X$ is a hydrogen atom or a hydrocarbon group optionally having one or more substituents, and M is a hydrogen atom or a metal atom; and
(iii) a metal oxide.

Examples of the oxidant (A) include metachloroperbenzoic acid, hydrogen peroxide, peracetic acid, perbenzoic acid, tert-butyl hydroperoxide, cumene hydroperoxide, potassium persulfate, a potassium hydrogen persulfate-potassium hydrogen sulfate-potassium sulfate mixture, permanganic acid, dichromic acid, tungsten oxide, ruthenium oxide, antimony oxide, osmium oxide, and sulfur trioxide.

Preferable examples of the oxidant (A) include metachloroperbenzoic acid, hydrogen peroxide, peracetic acid, perbenzoic acid, tert-butyl hydroperoxide, cumene hydroperoxide, potassium persulfate, and a potassium hydrogen persulfate-potassium hydrogen sulfate-potassium sulfate mixture.

More preferable examples of the oxidant (A) include m-chloroperbenzoic acid.

These can be used singly, or in combination of two or more.

The amount of the oxidant for use in step A may be typically 0.1 to 40 mol, and preferably 0.5 to 30 mol, per mol of the compound (2).

The hypervalent-iodine aromatic compound (1a) is preferably a compound represented by formula (p1):

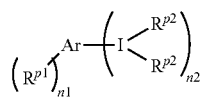

(p1)

wherein
Ar is an aromatic ring,
$R^{p1}$ is independently in each occurrence
  an alkyl group,
  an alkoxy group,
  a group: —O—$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a halogen atom,
  a cyano group,
  a nitro group,
  a carboxylic acid group, or
  a sulfonic acid group;
$R^{p2}$ is independently in each occurrence
  an alkyl group,
  an alkoxy group,
  a group: —O—$(CH_2)_g$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a group: —$(CH_2)_g$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a halogen atom,
  a cyano group,
  a nitro group,
  a carboxylic acid group,
  a sulfonic acid group,
  a hydroxy group, or
  a phosphoryloxy group; or
two $R^{p2}$ groups bonded to one iodine atom together optionally form =O;
n1 is a number greater than or equal to 0;
n2 is a number greater than or equal to 1; and
the sum of n1 and n2 is within the range of 1 to 11.
The aromatic iodine compound (1b) is preferably a compound represented by formula (p1'):

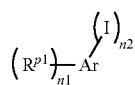

(p1')

wherein
Ar is an aromatic ring;
$R^{p1}$ is independently in each occurrence
  an alkyl group,
  an alkoxy group,
  a group: —O—$(CH_2)$—$NR_3X$, wherein q is a number greater than or equal to 1; R is independently, in each occurrence, H or a $C_1$-$C_{20}$ alkyl group; and X is a halogen atom, an arylsulfonyloxy group, or an alkylsulfonyloxy group,
  a group: —$(CH_2)_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
  a halogen atom,
  a cyano group,
  a nitro group,
  a carboxylic acid group, or
  a sulfonic acid group;
n1 is 0 to the maximum substitutable number (e.g., a number of 0 to 5); and
n2 is a number of 1 to 6.
As can typically be understood by a person skilled in the art, the maximum substitutable number for n1 varies depending on n2.
In structural formula (p1), $R^{p1}$ preferably represents, in each occurrence, independently an alkyl group optionally substituted with one or more fluorine atoms, an alkoxy group optionally substituted with one or more fluorine atoms, a halogen atom, a carboxylic acid group, or a sulfonic acid group.
In structural formula (p1'), $R^{p1}$ preferably represents, in each occurrence, independently an alkyl group optionally substituted with one or more fluorine atoms, an alkoxy group optionally substituted with one or more fluorine atoms, a halogen atom, a carboxylic acid group, or a sulfonic acid group.
The number of fluorine atoms as substituents may be within the range of 1 to the maximum substitutable number. Specific examples of the number of fluorine atoms as substituents include 1, 2, 3, 4, 5, 6, 7, 8, and 9.
In structural formula (p1), $R^{p2}$ preferably represents, in each occurrence, independently a halogen atom, an acetic acid group, a trifluoroacetic acid group, a tosic acid group, a hydroxy group, a phosphoryloxy group, a trifluoromethanesulfonic acid group, a propionic acid group, a 3,3,3-trifluoropropionic acid group, a perfluoropropionic acid group, a perfluorobutyric acid group, or a methanesulfonic acid group.
In the present specification, the term "acid group" refers to an atom or atomic group formed by removing one hydrogen atom that can be ionized as a hydrogen ion from a molecule of an organic or inorganic acid. Specifically, for example, a carboxylic acid group can include an acetic acid group; and an acetic acid group can be —$OCOCH_3$ (acetyloxy group) in the present specification.
The reaction in step A may be performed in the presence or absence of a solvent. The solvent may be a nonpolar solvent or a polar solvent. Specifically, an example of the solvent may be a nonpolar solvent or a polar solvent. The solvent may be an aromatic compound, an alcohol, an ether, a nitrogen-containing polar organic compound, nitrile, a halogenated hydrocarbon, an aliphatic hydrocarbon, a fluorine-based solvent, other solvents, or a combination of these solvents.
Examples of aromatic compounds as such a solvent include anisole, benzene, toluene, xylene, and ethyl benzene. Preferable examples include benzene and toluene.
Examples of alcohols as such a solvent include methanol, ethanol, n-propanol, isopropanol, n-butanol, pentanol, hexanol, ethylene glycol, diethylene glycol, triethylene glycol, tetraethylene glycol, polyethylene glycol, propylene glycol, dipropylene glycol, tripropylene glycol, polypropylene glycol, trimethylene glycol, and hexane triol. Preferable examples include methanol and ethanol.

Examples of ethers as such a solvent include diethyl ether, dibutyl ether, tetrahydrofuran, tetrahydropyran, dioxane, dimethoxyethane, diethylene glycol diethyl ether, ethylene glycol monomethyl ether, ethylene glycol monoethyl ether, diethylene glycol monomethyl ether, diethylene glycol monoethyl ether, propylene glycol monomethyl ether (PGME; another name therefor is 1-methoxy-2-propanol), propylene glycol monoethyl ether, triethylene glycol dimethyl ether, triethylene glycol diethyl ether, tetraethylene glycol dimethyl ether, and tetraethylene glycol diethyl ether. Preferable examples include diethyl ether and tetrahydrofuran.

Examples of nitrogen-containing polar organic compounds as such a solvent include N,N-dimethylformamide, N,N-dimethylacetamide, N-methyl-2-pyrrolidone, 2-pyrrolidone, and 1,3-dimethyl-2-imidazolidinone. Preferable examples include N,N-dimethylformamide, N,N-dimethylacetamide, and N-methyl-2-pyrrolidone.

Examples of nitriles as such a solvent include acetonitrile, propionitrile, butyronitrile, isobutyronitrile, benzonitrile, and adiponitrile. Preferable examples include acetonitrile.

Examples of halogenated hydrocarbons as such a solvent include dichloromethane, dichloroethane, chloroform, carbon tetrachloride, tetrachloroethane, trichloroethane, chlorobenzene, dichlorobenzene, and chlorotoluene. Preferable examples include dichloromethane and chloroform.

Examples of aliphatic hydrocarbons as such a solvent include hexane, cyclohexane, heptane, octane, nonane, decane, undecane, dodecane, and mineral spirits. Preferable examples include cyclohexane and heptane.

Examples of fluorine-based solvents include perfluorobenzene, trifluorotoluene, ditrifluorobenzene, and trifluoroethanol. Preferable examples include perfluorobenzene and trifluoroethanol.

Examples of other solvents include acetic acid, dimethyl sulfoxide, sulfolane, and water.

These solvents may be used singly, or in a combination of two or more.

The amount of the solvent may be, for example, typically 0 to 200 parts by mass, preferably 0 to 100 parts by mass, and more preferably 0 to 50 parts by mass, per part by mass of the organic compound (1), which is the substrate in the production method according to the present disclosure.

The temperature in step A may be typically −78 to 200° C., preferably −10 to 100° C., and more preferably 0 to 100° C.

The time period in step A may be typically 0.1 to 72 hours, preferably 0.1 to 48 hours, more preferably 0.2 to 24 hours, and still more preferably 0.5 to 12 hours.

The production method according to the present disclosure can achieve a starting material conversion of preferably 10% or more, more preferably 20% or more, and still more preferably 30% or more.

The production method according to the present disclosure can achieve a selectivity for the target compound of preferably 50% or more, and more preferably 60% or more.

The production method according to the present disclosure can achieve a yield of the target compound of preferably 10% or more, more preferably 20% or more, and still more preferably 30% or more.

2. Fluorinated Organic Compound

An embodiment according to the present disclosure is a fluorinated organic compound represented by formula (1-1):

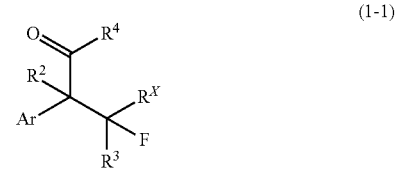

(1-1)

wherein

Ar represents an aromatic hydrocarbon group optionally having one or more substituents or an aromatic heterocyclic group optionally having one or more substituents;

$R^2$ represents hydrogen, halogen, or an organic group;

$R^3$ represents hydrogen, halogen, or an organic group;

$R^4$ represents an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents; and $R^X$ represents hydrogen or fluoro.

Preferable embodiments of this compound can be understood from the preferable embodiments explained for the production method.

In an embodiment, $R^X$ is preferably fluoro. In another embodiment, $R^X$ is preferably hydrogen.

EXAMPLES

The present disclosure is described in more detail below with reference to Examples. However, the present disclosure is not limited to the Examples.

In the Examples, the term "yield" refers to an isolated yield, unless specified otherwise.

The symbols and abbreviations used in the Examples are listed below.

TEA: triethylamine
DCM: dichloromethane
Ph: phenyl
Ac: acetyl
Py: pyridine
m-CPBA: meta-chloroperbenzoic acid Example 1a Fluorination Reaction 1

PhIO (1.3 eq.), Py·HF (25 eq.), and $CH_2Cl_2$ were placed in a vessel, and stirred at room temperature. (E)-chalcone (1 mmol) and $CH_2Cl_2$ were added thereto at room temperature, and the mixture was stirred at room temperature for 7 hours. The reaction mixture was then neutralized with an aqueous solution of sodium hydrogen carbonate, followed by extracting the aqueous layer with $CH_2Cl_2$ three times. The obtained organic layer was dried over $Na_2SO_4$, and evaporation was performed. Thereafter, silica gel column chromatography was performed, thereby isolating a target product, 3,3-difluoro-1,2-diphenylpropan-1-one, at a yield of 82%.

Example 1b

The procedure of Example 1a was repeated, except that the starting material was changed from the (E)-chalcone to (E)-4-phenylbut-3-en-2-one, thereby obtaining 4,4-difluoro-3-phenylbutan-2-one at a yield of 67%.

Example 1c

The procedure of Example 1a was repeated, except that the starting material was changed from the (E)-chalcone to (E)-4,4-dimethyl-1-phenylpent-1-en-3-one, thereby obtaining 1,1-difluoro-4,4-dimethyl-2-phenylpentan-3-one at a yield of 80%.

Example 1d

The procedure of Example 1a was repeated, except that the starting material was changed from the (E)-chalcone to (E)-1-(4-nitrophenyl)-3-phenylprop-2-en-1-one, thereby obtaining 3,3-difluoro-1-(4-nitrophenyl)-2-phenylpropan-1-one at a yield of 86%.

Example 1e

The procedure of Example 1a was repeated, except that the starting material was changed from the (E)-chalcone to (E)-1-(4-methoxyphenyl)-3-phenylprop-2-en-1-one, thereby obtaining 3,3-difluoro-1-(4-methoxyphenyl)-2-phenylpropan-1-one at a yield of 71%.

Example 1f

The procedure of Example 1a was repeated, except that the starting material was changed from the (E)-chalcone to (E)-1-(naphthalen-2-yl)-3-phenylprop-2-en-1-one, thereby obtaining 3,3-difluoro-1-(naphthalen-2-yl)-2-phenylpropan-1-one at a yield of 63%.

Example 1g

The procedure of Example 1a was repeated, except that the starting material was changed from the (E)-chalcone to (E)-3-phenyl-1-(thiophen-2-yl)prop-2-en-1-one, thereby obtaining 3,3-difluoro-2-phenyl-1-(thiophen-2-yl)propan-1-one at a yield of 80%.

Example 1h

The procedure of Example 1a was repeated, except that the starting material was changed from the (E)-chalcone to 3-(4-chlorophenyl)-1-(4-methoxyphenyl)prop-2-en-1-one, thereby obtaining 2-(4-chlorophenyl)-3,3-difluoro-1-(4-methoxyphenyl)propan-1-one at a yield of 66%.

Example 1i

The procedure of Example 1a was repeated, except that the starting material was changed from the (E)-chalcone to 1-phenylnon-1-en-3-one, thereby obtaining 1,1-difluoro-2-phenylnonan-3-one at a yield of 67%.

Example 1j

The procedure of Example 1a was repeated, except that the starting material was changed from the (E)-chalcone to 1-(4-chlorophenyl)-3-phenylprop-2-en-1-one, thereby obtaining 1-(4-chlorophenyl)-3,3-difluoro-2-phenylpropan-1-one at a yield of 86%.

Example 1k

The procedure of Example 1a was repeated, except that the starting material was changed from the (E)-chalcone to N-(4-cinnamoylphenyl)acetamide, thereby obtaining N-(4-(3,3-difluoro-2-phenylpropanoyl)phenyl)acetamide at a yield of 77%.

Example 1l

The procedure of Example 1a was repeated, except that the starting material was changed from the (E)-chalcone to 1-phenyl-3-(p-tolyl)prop-2-en-1-one, thereby obtaining 3,3-difluoro-1-phenyl-2-(p-tolyl)propan-1-one at a yield of 52%.

Example 1m

The procedure of Example 1a was repeated, except that the starting material was changed from the (E)-chalcone to 3-(4-chlorophenyl)-1-phenylprop-2-en-1-one, thereby obtaining 2-(4-chlorophenyl)-3,3-difluoro-1-phenylpropan-1-one at a yield of 80%.

Example 1n

The procedure of Example 1a was repeated, except that the starting material was changed from the (E)-chalcone to 3-(4-fluorophenyl)-1-phenylprop-2-en-1-one, thereby obtaining 3,3-difluoro-2-(4-fluorophenyl)-1-phenylpropan-1-one at a yield of 81%.

Example 1o

The procedure of Example 1a was repeated, except that the starting material was changed from the (E)-chalcone to 1-(4-chlorophenyl)-3-(p-tolyl)prop-2-en-1-one, thereby obtaining 1-(4-chlorophenyl)-3,3-difluoro-2-(p-tolyl)propan-1-one at a yield of 58%.

Example 1p

The procedure of Example 1a was repeated, except that the starting material was changed from the (E)-chalcone to 1,3-diphenylbut-2-en-1-one, thereby obtaining 3,3-difluoro-2-methyl-1,2-diphenylpropan-1-one at a yield of 72%.

Example 1q

The procedure of Example 1a was repeated, except that the starting material was changed from the (E)-chalcone to 1-phenyl-3-(p-tolyl)but-2-en-1-one, thereby obtaining 3,3-difluoro-2-methyl-1-phenyl-2-(p-tolyl)propan-1-one at a yield of 60%.

Example 1r

The procedure of Example 1a was repeated, except that the starting material was changed from the (E)-chalcone to 7-phenyl-8,9-dihydro-5H-benzo[7]annulen-5-one, thereby obtaining 2-(difluoromethyl)-2-phenyl-3,4-dihydronaphthalen-1(2H)-one at a yield of 49%.

Example 2a

Fluorination Reaction 2

4-Iodotolene (20 mol %), mCPBA (1.3 eq.), and $CH_2Cl_2$ were placed in a vessel. Py·HF (40 eq.) and $CH_2Cl_2$ were added thereto, followed by stirring at room temperature for 15 minutes. (E)-chalcone (0.5 mmol) and $CH_2Cl_2$ were added thereto at room temperature, and the mixture was stirred at room temperature for 24 hours. Thereafter, the aqueous layer was extracted with $CH_2Cl_2$ three times. The organic layer was dried over $Na_2SO_4$, and evaporation was performed. Silica gel column chromatography was performed, thereby isolating a target product, 3,3-difluoro-1,2-diphenylpropan-1-one, at a yield of 68%.

Example 2b

The procedure of Example 1a was repeated, except that the starting material was changed from the (E)-chalcone to (E)-4-phenylbut-3-en-2-one, thereby obtaining 4,4-difluoro-3-phenylbutan-2-one at a yield of 32%.

Example 2c

The procedure of Example 1a was repeated, except that the starting material was changed from the (E)-chalcone to (E)-4,4-dimethyl-1-phenylpent-1-en-3-one, thereby obtaining 1,1-difluoro-4,4-dimethyl-2-phenylpentan-3-one at a yield of 73%.

Example 2d

The procedure of Example 1a was repeated, except that the starting material was changed from the (E)-chalcone to (E)-1-(4-nitrophenyl)-3-phenylprop-2-en-1-one, thereby obtaining 3,3-difluoro-1-(4-nitrophenyl)-2-phenylpropan-1-one at a yield of 67%.

Example 2e

The procedure of Example 1a was repeated, except that the starting material was changed from the (E)-chalcone to (E)-1-(4-methoxyphenyl)-3-phenylprop-2-en-1-one, thereby obtaining 3,3-difluoro-1-(4-methoxyphenyl)-2-phenylpropan-1-one at a yield of 62%.

Example 2f

The procedure of Example 1a was repeated, except that the starting material was changed from the (E)-chalcone to (E)-1-(naphthalen-2-yl)-3-phenylprop-2-en-1-one, thereby obtaining 3,3-difluoro-1-(naphthalen-2-yl)-2-phenylpropan-1-one at a yield of 26%.

Example 2g

The procedure of Example 1a was repeated, except that the starting material was changed from the (E)-chalcone to (E)-3-phenyl-1-(thiophen-2-yl)prop-2-en-1-one, thereby obtaining 3,3-difluoro-2-phenyl-1-(thiophen-2-yl)propan-1-one at a yield of 85%.

Example 2h

The procedure of Example 1a was repeated, except that the starting material was changed from the (E)-chalcone to (E)-3-(4-chlorophenyl)-1-(4-methoxyphenyl)prop-2-en-1-one, thereby obtaining 2-(4-chlorophenyl)-3,3-difluoro-1-(4-methoxyphenyl)propan-1-one at a yield of 56%.

Example 3a

Fluorination Reaction 3
PhIO (1.3 eq.), Py·HF (20 eq.), and $CH_2Cl_2$ were placed in a vessel, and stirred at room temperature. Ethyl cinnamate (1 mmol) and $CH_2Cl_2$ were then added thereto at temperature, and the mixture was stirred at room temperature for 7 hours. The reaction product was then neutralized with an aqueous solution of sodium hydrogen carbonate, and the aqueous layer was extracted with $CH_2Cl_2$. The organic layer was dried over $Na_2SO_4$, and evaporation was performed. Thereafter, silica gel column chromatography was performed, thereby isolating a target product, ethyl 3,3-difluoro-2-phenylpropanoate, at a yield of 77%.

Example 3b

The procedure of Example 3a was repeated, except that the starting material was changed from the ethyl cinnamate to ethyl (E)-3-(p-tolyl)acrylate, thereby obtaining ethyl 3,3-difluoro-2-(p-tolyl)propanoate at a yield of 80%.

Example 3c

The procedure of Example 3a was repeated, except that the starting material was changed from the ethyl cinnamate to ethyl (E)-3-(o-tolyl)acrylate, thereby obtaining ethyl 3,3-difluoro-2-(o-tolyl)propanoate at a yield of 85%.

Example 3d

The procedure of Example 3a was repeated, except that the starting material was changed from the ethyl cinnamate to ethyl (E)-3-(4-fluorophenyl)acrylate, thereby obtaining ethyl 3,3-difluoro-2-(4-fluorophenyl)propanoate at a yield of 77%.

Example 4a

Fluorination Reaction 4
PhIO (1.4 eq.), Py·HF (20 eq.), and $CH_2Cl_2$ were stirred at room temperature. Thereafter, (E)-3-phenylprop-2-en-1-ol (1 mmol) and $CH_2Cl_2$ were added thereto at room temperature, followed by stirring at −45° C. for 2 hours. The reaction product was then neutralized with an aqueous solution of sodium hydrogen carbonate, followed by extracting the aqueous layer with $CH_2Cl_2$ three times. The obtained organic layer was dried over $Na_2SO_4$, and evaporation was further performed. Thereafter, silica gel column chromatography was performed, thereby isolating a target product, 3,3-difluoro-2-phenylpropan-1-ol, at a yield of 52%.

Example 4b

The procedure of Example 4a was repeated, except that the starting material was changed from the (E)-3-phenylprop-2-en-1-ol to (E)-3-(o-tolyl)prop-2-en-1-ol, thereby obtaining 3,3-difluoro-2-(o-tolyl)propan-1-ol at a yield of 47%.

Example 4c

The procedure of Example 4a was repeated, except that the starting material was changed from the (E)-3-phenyl-prop-2-en-1-ol to (E)-3-(4-fluorophenyl)prop-2-en-1-ol, thereby obtaining 3,3-difluoro-2-(4-fluorophenyl)propan-1-ol at a yield of 38%.

Example 4d

The procedure of Example 4a was repeated, except that the starting material was changed from the (E)-3-phenylprop-2-en-1-ol to (E)-3-phenylbut-2-en-1-ol, thereby obtaining 3,3-difluoro-2-phenylbutan-1-ol at a yield of 54%.

Example 5a

PhIO (1.4 eq.), Py·HF (20 eq.), and CH$_2$Cl$_2$ were placed in a vessel, and stirred at −45° C. Thereafter, 3-(o-tolyl)prop-2-en-1-ol (1 mmol) was added thereto, followed by stirring at −45° C. for 2 hours. The reaction product was then neutralized with an aqueous solution of sodium hydrogen carbonate, followed by extracting the aqueous layer with CH$_2$Cl$_2$. The organic layer was dried over Na$_2$SO$_4$, and evaporation was performed. Thereafter, silica gel column chromatography was performed, thereby isolating a target product, 3,3-difluoro-2-(o-tolyl)propan-1-ol, at a yield of 47%.

Example 5b

The procedure of Example 5a was repeated, except that the starting material was changed from the 3-(o-tolyl)prop-2-en-1-ol to 3-(p-tolyl)prop-2-en-1-ol, thereby obtaining 3,3-difluoro-2-(p-tolyl)propan-1-ol at a yield of 38%.

Example 5c

The procedure of Example 5a was repeated, except that the starting material was changed from the 3-(o-tolyl)prop-2-en-1-ol to 3-(4-fluorophenyl)prop-2-en-1-ol, thereby obtaining 3,3-difluoro-2-(4-fluorophenyl)propan-1-ol at a yield of 38%.

Example 5d

The procedure of Example 5a was repeated, except that the starting material was changed from the 3-(o-tolyl)prop-2-en-1-ol to 3-(4-chlorophenyl)prop-2-en-1-ol, thereby obtaining 2-(4-chlorophenyl)-3,3-difluoropropan-1-ol at a yield of 48%.

Example 5e

The procedure of Example 5a was repeated, except that the starting material was changed from the 3-(o-tolyl)prop-2-en-1-ol to 3-(4-bromophenyl)prop-2-en-1-ol, thereby obtaining 2-(4-bromophenyl)-3,3-difluoropropan-1-ol at a yield of 33%.

Example 5f

The procedure of Example 5a was repeated, except that the starting material was changed from the 3-(o-tolyl)prop-2-en-1-ol to 3-phenylbut-2-en-1-ol, thereby obtaining 3,3-difluoro-2-phenylbutan-1-ol at a yield of 54%.

The invention claimed is:
1. A method for producing a fluorinated organic compound represented by formula (1):

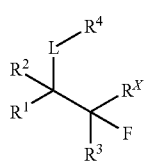

(1)

wherein
R$^1$ represents an aromatic hydrocarbon group optionally having one or more substituents, or an aromatic heterocyclic group optionally having one or more substituents,
R$^2$ represents hydrogen, halogen, an alkyl group optionally having one or more substituents, an aryl group optionally having one or more substituents, a non-aromatic heterocyclic group optionally having one or more substituents, or a heteroaryl group optionally having one or more substituents,
R$^3$ represents hydrogen, or an alkyl group optionally having one or more substituents,
L represents —CO—,
R$^4$ represents hydrogen, halogen, hydroxyl, an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents, and
R$^X$ represents fluoro,
the method comprising step A of reacting an alkene compound represented by formula (2):

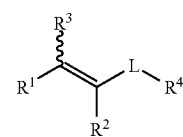

(2)

wherein the steric configuration of a single bond indicated by a wavy line with respect to a double bond to which the single bond is connected is in E configuration or Z configuration, or a mixture of E configuration and Z configuration in any ratio, and other alphabetical symbols are as defined above,
with a fluorine source that is a fluorine source (3a) represented by formula MF$_n$ wherein M represents H, a metal of Group 1 of the periodic table, or a metal of Group 2 of the periodic table; and n is 1 or 2
in the presence of a hypervalent-iodine aromatic compound (1a), or
in the presence of an aromatic iodine compound (1b) and an oxidant (A) to fluorinate the alkene compound,
wherein the hypervalent-iodine aromatic compound (1a) is a compound represented by formula (p1):

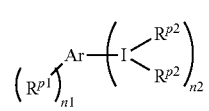

(p1)

wherein
Ar is an aromatic ring,
R$^{p1}$ is independently in each occurrence
an alkyl group,
an alkoxy group,
a group: —O—(CH$_2$)$_q$—NR$_3$X, wherein q is a number greater than or equal to 1; R is H or a C$_1$-C$_{20}$ alkyl group; and X is a halogen atom, an arylsulfonyloxy group, or an alkylsulfonyloxy group, a group: —($CH_2$)$_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a halogen atom,
a cyano group,
a nitro group,
a carboxylic acid group, or
a sulfonic acid group;
$R^{p2}$ is independently in each occurrence
an alkyl group,
an alkoxy group,
a group: —O—($CH_2$)$_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a group: —($CH_2$)$_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a halogen atom,
a cyano group,
a nitro group,
a carboxylic acid group,
a sulfonic acid group,
a hydroxy group, or
a phosphoryloxy group; or
two $R^{p2}$ groups bonded to one iodine atom together optionally form =O;
n1 is a number greater than or equal to 0;
n2 is a number greater than or equal to 1; and
the sum of n1 and n2 is within the range of 1 to 11,
wherein the aromatic iodine compound (1b) is a compound represented by formula (p1'):

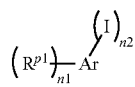

(p1')

wherein
Ar is an aromatic ring;
$R^{p1}$ is independently in each occurrence
an alkyl group,
an alkoxy group,
a group: —O—($CH_2$)$_q$—$NR_3X$, wherein q is a number greater than or equal to 1; R is independently, in each occurrence, H or a $C_1$-$C_{20}$ alkyl group; and X is a halogen atom, an arylsulfonyloxy group, or an alkylsulfonyloxy group,
a group: —($CH_2$)$_q$—$NR_3X$, wherein q is a number greater than or equal to 1; R is H or a $C_1$-$C_{20}$ alkyl group; and X is a halogen atom, an arylsulfonyloxy group, or an alkylsulfonyloxy group,
a halogen atom,
a cyano group,
a nitro group,
a carboxylic acid group, or
a sulfonic acid group;
n1 is 0 to the maximum substitutable number; and
n2 is a number of 1 to 6, and
wherein the oxidant (A) is one or more members selected from the group consisting of:
(i) a compound represented by formula: $R^XCOOOM$ wherein, in formula $R^XCOOOM$, $R^X$ is a hydrocarbon group optionally having one or more substituents, and
M is a hydrogen atom or a metal atom;
(ii) a compound represented by formula: $R^XOOM$ wherein, in formula $R^XOOM$, $R^X$ is a hydrogen atom or a hydrocarbon group optionally having one or more substituents, and
M is a hydrogen atom or a metal atom; and
(iii) a metal oxide.

2. The production method according to claim 1, wherein $R^2$ represents hydrogen.

3. The production method according to claim 1, wherein $R^3$ represents hydrogen.

4. The production method according to claim 1, wherein $R^4$ represents hydrogen or an aliphatic hydrocarbon group optionally having one or more substituents, an aromatic hydrocarbon group optionally having one or more substituents, an aliphatic heterocyclic group optionally having one or more substituents, or an aromatic heterocyclic group optionally having one or more substituents.

* * * * *